United States Patent [19]

Kronman

[11] 4,391,010
[45] Jul. 5, 1983

[54] DISPOSABLE DRAW SHEET

[75] Inventor: Albert F. Kronman, Locust Valley, N.Y.

[73] Assignee: Hosposable Products Inc., Bound Brook, N.J.

[21] Appl. No.: 293,864

[22] Filed: Aug. 18, 1981

[51] Int. Cl.³ .................. A47G 9/00; A61G 12/00
[52] U.S. Cl. ............................................ 5/484; 5/485; 5/500
[58] Field of Search .............. 5/484, 485, 500, 482, 5/483, 486, 487, 493, 494, 495, 496, 497, 498, 499, 501, 502; D6/258–263

[56] References Cited

U.S. PATENT DOCUMENTS

| 1,562,809 | 11/1925 | Thompson | 5/484 |
| 2,414,927 | 1/1947 | Chapman | 5/354 |
| 3,394,416 | 7/1968 | Hale | 5/354 |
| 3,454,969 | 7/1969 | Lundberg |  |
| 3,646,524 | 3/1922 | Zipf | 5/484 |
| 4,064,577 | 12/1977 | Walters | 5/484 |

FOREIGN PATENT DOCUMENTS 275440  8/1927  United Kingdom .................... 5/498

Primary Examiner—Alexander Grosz
Attorney, Agent, or Firm—Albert F. Kronman

[57] ABSTRACT

A disposable draw sheet for use on bed mattresses in which a thin sheet of liquid impervious material supports a liquid absorbent material layer. The liquid impervious sheet is wide enough to be tucked under each side of the mattress. Pockets formed by doubling the longitudinal margins of the sheet back upon themselves and tacking them at spaced discrete areas provide easy application and removal of the draw sheets.

8 Claims, 7 Drawing Figures

DISPOSABLE DRAW SHEET

BACKGROUND OF THE INVENTION

1. Field of the Invention

This invention relates to draw sheets for bedding, and more particularly to disposable draw sheets made of lightweight plastic to the top of which is secured a liquid absorbent layer or pad.

2. Description of the Prior Art

Prior art disposable draw sheets such as are shown in U.S. Pat. Nos. 3,308,488 issued to Schoonman Mar. 14, 1967 and 3,646,624 issued to Zipf Mar. 7, 1972 have been made of very thin sheets of plastic material such as polyolefins, particularly polyethylene, which is an inexpensive, water-proof material. Because of the necessity for keeping the cost of disposable draw sheets to a minimum, the polyethylene sheeting is usually made as thin as possible, short of its being able to function for the purpose intended. The result is that such draw sheets are difficult to handle particularly when a nurse or hospital attendant attempts to place these articles upon a mattress and tuck them under the mattress so that they are secured in place. The disposable draw sheets are delivered folded and the folded over portions stick together so that the thin edges are difficult to locate merely by feeling for them. It will be understood that in hospital use these draw sheets are placed upon the mattress with the absorbent side facing up. The nurse then reaches underneath the folded draw sheet, has to locate the edge of the sheet which is folded underneath major portions of the sheet, pull it out until it drapes over the edge of the mattress and tuck it beneath the mattress. The patient, meanwhile, has been rolled away, at least partially, from the folded draw sheet and once one side is tucked in, the patient is rolled to the opposite side while the nurse once again reaches under the draw sheet for the very thin edge of the plastic. In addition, when attempting to push the plastic underneath the mattress, the thin plastic material is hard to force under the mattress, without tearing, to produce a tight fold-free surface for the patient.

In the manufacture of U.S. Pat. No. 3,646,624 the plastic material is made in the form of an elongated tube in which the opposed sides are brought together in almost abutting relationship beneath the portion of the plastic to which the absorbent pad is secured. This structure makes it even more difficult for the user to locate the edge of the sheet so that it can be pulled out from underneath the draw sheet.

SUMMARY OF THE INVENTION

A disposable draw sheet according to the present invention consists of a base sheet of thin, inexpensive plastic, such as polyethylene, to the top of which there is secured a liquid absorbent pad preferably of some non-woven material. The pad is of a width which will extend substantially across the width of the mattress and of a length which will extend beneath the patient's torso. The plastic material is substantially wider than the absorbent pad so that it may be tucked under the mattress on each side thereof to hold the draw sheet tightly in place. In order to facilitate locating, withdrawing and tucking of each of the longitudinal margins of the sheet, the said margins are folded back upon themselves and tucked or bonded together at discrete areas to form a pocket into which the nurse or user can thrust both hands.

It is therefore an object of the present invention to provide a disposable draw sheet which is easier to handle and capable of tighter tucking then prior art devices. A further object of the present invention is to provide a disposable draw sheet with improved tucking capacity without substantially increasing the cost of the article.

BRIEF DESCRIPTION OF THE DRAWINGS

In the accompanying drawing forming part hereof similar elements have been given the same reference numerals, in which drawing.

DESCRIPTION OF THE PREFERRED EMBODIMENTS

Figure 1:
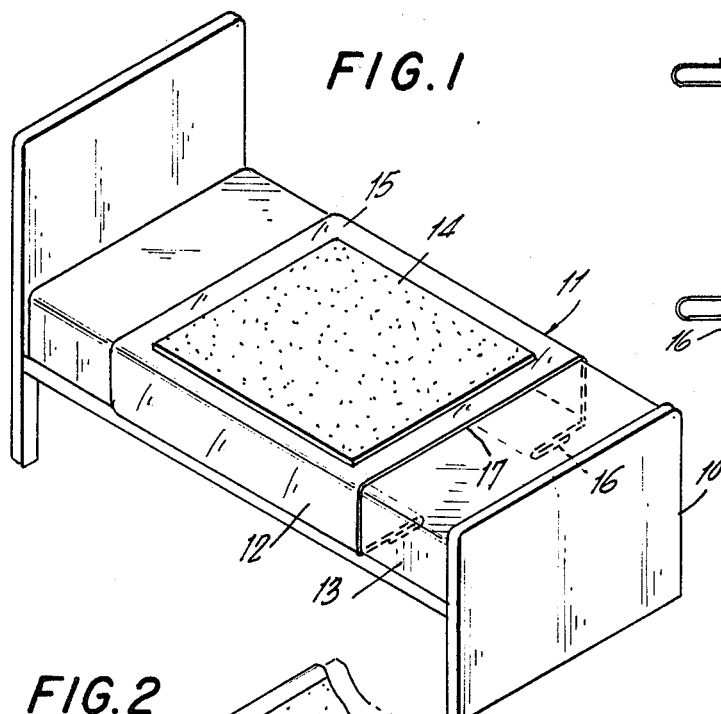
FIG. 1 is a perspective view of a bed employing the draw sheet of the present invention.

Referring to the drawings, 10 indicates a bed having a disposable draw sheet 11 thereon, made in accordance with the present invention. The draw sheet 11 consists of a sheet 12 of some suitable plastic material such as polyethylene, polypropylene and the like. The plastic sheet 12 is of a width which is substantially wider than the mattress 13 of the bed so that it may be tucked under the mattress in the customary manner. In the use of the draw sheet, it is essential that it be tucked beneath the mattress in such manner that it will be held tightly in place without wrinkles being developed on the surface upon which a person lies. It is also important that the draw sheet be stretched tightly across the surface of the mattress 13 when it is applied to the mattress so that there are no wrinkles left in the said draw sheet at that time.

A layer of some suitable liquid absorbing material 14 is secured to the upper surface 15 of the plastic sheet 12. The absorbent material 14 may be made of any light, inexpensive material such as cotton fibers, woven or non-woven cellulosic fibers preferably having a high liquid absorbency. The layer of absorbent material is of a width which is somewhat less than the width of the mattress and long enough to underlie the torso of the person who will rest upon the draw sheet.

Figure 6:
FIG. 6 is a diagrammatical cross-sectional view of a draw sheet of the prior art.
Figure 7:
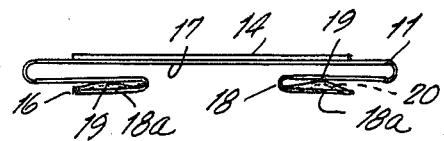
FIG. 7 is a view similar to FIG. 6 showing the draw sheet of the present invention.
Figure 2:
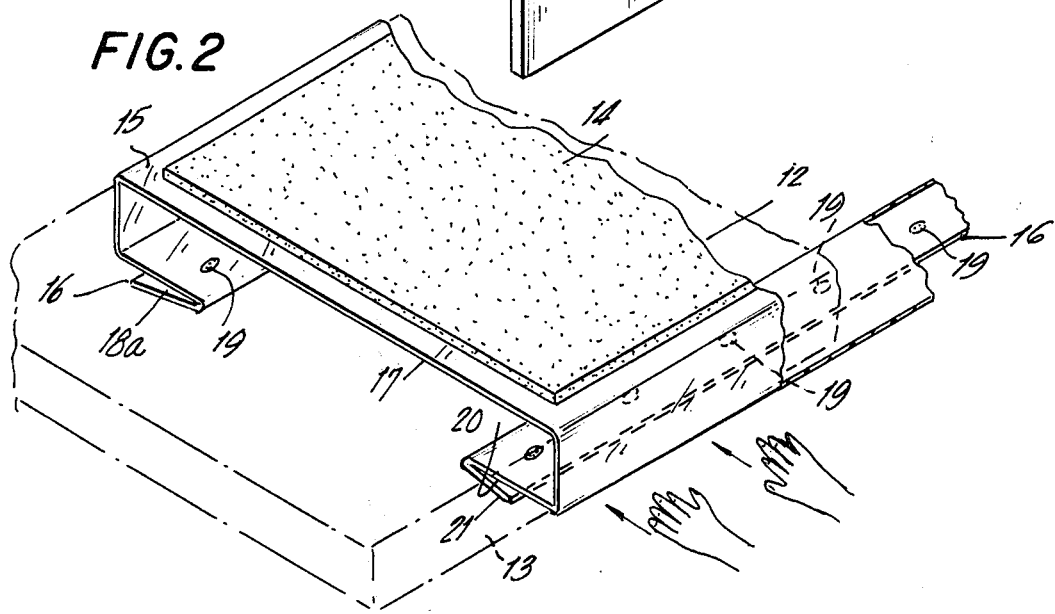
FIG. 2 is a fragmentary view, somewhat enlarged, of the mattress and draw sheet shown in FIG. 1.
Figures 3, 4:
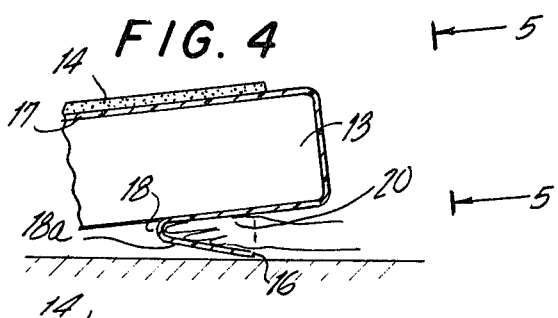
FIG. 3 is a cross-sectional view of a portion of the mattress and draw sheet made in accordance with the present invention.
FIG. 4 is a view similar to FIG. 3 showing the manner in which the draw sheet is tucked into place.
Figure 5:
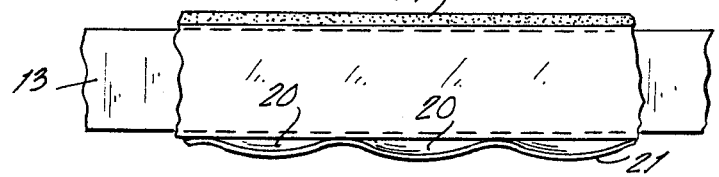
FIG. 5 is a view taken on Line 5,5 of FIG. 4 looking in the direction of the arrows.

In FIG. 6 there is illustrated a draw sheet made in accordance with the prior art illustrating its appearance, somewhat diagrammatically, before application to a mattress. It will be seen that the longitudinal edges 16 of the plastic sheet 12 are disposed beneath the upper portion of the draw sheet upon which the layer of absorbent material 14 is supported. These longitudinal edges are in close proximity, and actually lie in contact with the bottom surface 17 of the plastic sheet 12. In the manufacture of disposable draw sheets, the edges 16 often abut one another or slightly overlap. The showing of FIG. 6 further illustrates the disposition of a prior art draw sheet when it is first placed upon a mattress and prior to being tucked underneath the mattress in the manner illustrated in FIG. 1. Referring to FIG. 7, there is shown a somewhat diagrammatic view of a draw sheet made in accordance with the present invention and prior to being tucked beneath a mattress. It will be seen that the longitudinal margins 18a of the present invention are doubled back upon themselves and upon the outer or top surface 15 of the plastic sheet 12 to provide a thickened inner edge 18 which may be located more easily and grasped by a nurse or attendant in carrying out the steps of the tucking operation. The first step in the tucking operation is to pull one of the sides of the draw sheet out from under the folded draw sheet shown in FIG. 7. Since the draw sheet is in the position shown in FIG. 7 at this juncture, locating the longitudinal edge portion must be done by feeling for it beneath the draw sheet. Having located the thickened edge 18, it is pulled out from beneath the draw sheet until it hangs over the side of mattress 13. In the prior art device shown in FIG. 6 the nurse then pushes the plastic sheet which overhangs the mattress beneath the mattress using hands and fingertips until it is sufficiently under the mattress to be firmly held by the mattress against a spring or box spring upon the bed. Since the plastic sheet 12 is necessarily of the thinnest gauge possible for the purpose (of the order of one mil), the tucking operation may tear the sheet. In addition, it is often necessary to hold the mattress up with one hand and push the sheet in place with the other. As shown in FIGS. 2-7, the doubled back portion 21 of the longitudinal margins 18a of the thickened sheet is tacked or bonded by means of adhesives or heat welding at various points shown by the dotted lines 19 to form one or more pockets 20 in the doubled back portion. The tacked points 19 may be inwardly spaced from each end of the doubled back portion or at regular intervals as shown in FIGS. 2 and 5. In either case, the pockets facilitate tucking the draw sheet 11 by permitting the nurse or attendant the opportunity of placing hands into the pockets and guiding the free ends of the sheet beneath the mattress in the manner shown in FIG. 4. Two hands can be used and the mattress lifted on the backs of the user's hands during the tucking operation. It will be seen that the provision of the pockets 20 does not increase the size nor the cost of the draw sheet to any substantial degree. The doubled back portion 21 of the draw sheet also serves to anchor the sheet in place by preventing lateral slipping.

It is to be understood that the above described handling of the longitudinal margins of the sheet is repeated for the second or opposite side.

When it is desired to remove the draw sheet, the nurse can slip her hands beneath the doubled back portions 21 and easily locate the thickened inner edge portion 18 so that it can be pulled out from beneath the mattress. Since the thickened portion is being grasped there is less likelihood of tearing the thin plastic sheet and thus leaving portions of it beneath the mattress.

Having thus fully described the invention, what is desired to be claimed and secured by Letters Patent is:

1. A disposable draw sheet for application to the mattress of a bed comprising a thin sheet of liquid impervious material, a top surface, a bottom surface, longitudinal margins on said sheet and a sheet width substantially greater than that of the mattress to which it is to be applied so that said sheet margins may be tucked under said mattress on opposite sides thereof, a layer of liquid absorbent material carried by the top surface of the sheet across the midregion of said sheet, said absorbent material being of a width less than the top of the mattress, a doubled back portion on the longitudinal margins of the sheet, and means to secure the doubled back portion of the said margins to the top surface of the said sheet in at least two spaced discrete areas to form at least one pocket in each of the doubled back portions.

2. A draw sheet according to claim 1 in which the sheet is a plastic material.

3. A draw sheet according to claim 2 in which the doubled back securing means is a weld.

4. A draw sheet according to claim 1 in which the liquid absorbent material is made of cotton fibers bonded to the top surface of the sheet.

5. A draw sheet according to claim 1 in which the doubled back portion of the margins form a thickened inner edge on each of the said margins.

6. A draw sheet according to claim 1 in which the sheet has a thickness of the order of 1 mil.

7. A draw sheet according to claim 1 in which the doubled back securing means is an adhesive.

8. A draw sheet according to claim 1 in which the doubled back portion of the margins are secured at a plurality of spaced areas to form a series of pockets therebetween.

* * * * *